United States Patent [19]

Gough

[11] 4,133,878

[45] Jan. 9, 1979

[54] STABILIZED ORGANOTHIOPHOSPHORUS FORMULATIONS

[75] Inventor: Stanley T. D. Gough, Somerville, N.J.

[73] Assignee: Mobil Oil Corporation, New York, N.Y.

[21] Appl. No.: 833,840

[22] Filed: Sep. 16, 1977

Related U.S. Application Data

[63] Continuation of Ser. No. 642,958, Dec. 22, 1975, abandoned.

[51] Int. Cl.$^2$ ............................................... A01N 9/36
[52] U.S. Cl. ..................................... 424/225; 424/365
[58] Field of Search ................. 424/216, 225, 300, 365

[56] References Cited

U.S. PATENT DOCUMENTS

| | | | |
|---|---|---|---|
| 2,970,080 | 1/1961 | Oros et al. | 424/216 |
| 3,112,244 | 11/1963 | Goyette | 424/225 |
| 3,553,328 | 1/1971 | Koundakjian | 424/300 |

*Primary Examiner*—V. D. Turner
*Attorney, Agent, or Firm*—Charles A. Huggett; Hastings S. Trigg

[57] ABSTRACT

A composition comprising a pesticidal organothiophosphorus compound and a clay carrier in combination with a mixture of an alkylene glycol and an acid thereby providing compositions of high storage stability; said composition being useful, among other pesticidal control, for highly effective control of corn rootworm.

5 Claims, No Drawings

STABILIZED ORGANOTHIOPHOSPHORUS FORMULATIONS

CROSS REFERENCE TO RELATED APPLICATIONS

This application is a continuation of copending application Ser. No. 642,958, filed Dec. 22, 1975, now abandoned.

BACKGROUND OF THE INVENTION

1. Field of the Invention

This invention relates to compositions of matter comprising a pesticidal organothiophosphorus compound and a particulate clay carrier in admixture with a polyalkylene glycol and an acid which provide pesticidal compositions of high storage stability and which compositions are useful, among other pesticide controls, for highly effective control of corn rootworm.

2. Description of the Prior Art

Glycols have been previously used to stabilize organothiophosphorus compounds such as phosphorodithioates and phosphorodithioites when mixed with certain clay carriers, and it is also known to deactivate acid sites on various clay carriers or diluents for insecticidal compositions. For example, U.S. Pat. No. 2,970,080 relates to the use of certain polyalkylene (e.g., ethylene) glycols to stabilize some insecticidal compositions containing organic phosphates (e.g., phosphorodithioates). U.S. Pat. No. 2,868,688 relates to the use of nitrogeneous compounds (e.g., ammonium carbamate, urea, etc.) to deactivate acid sites on such clay carriers. The prior art also discloses the use of acids as deactivators of clay carriers; Sankyo-Japanese No. 62/15,648 relates to the use of fatty acids (e.g., $C_{14}$-$C_{18}$) to stabilize organophosphorus insecticides; S. Goto, I. Muta, R. Sato, Botyu-Kagaku 24-93108 (1959) also disclose such use of fatty acids.

J. A. Polon & E. W. Sawyer, J. Ag. Food Chem. 10–244 (1962) discuss the use of acid stabilizing agents to decrease the decomposition of such organophosphorus compounds as Malathion on high-sorptive clay carriers; also discussed is the use of glycols for similar purposes. However, no reference known to applicant discloses or teaches the joint use of glycols and acids as disclosed herein to stabilize organothiophosphorus compounds admixed with clay carriers.

DESCRIPTION OF THE PREFERRED EMBODIMENTS

The hereindescribed invention therefore relates to stabilized compositions of matter that are pesticidally and more particularly nematicidally and insecticidally effective comprising pesticidally effective amounts of an organothiophosphorus compound having the following general formula:

(RS)$_2$P(O)OR' wherein R' is selected from the group consisting of methyl and ethyl, R is selected from the group consisting of propyl and butyl when R' is methyl, and R is propyl when R' is ethyl, a solid particulate clay carrier therefor and a stabilizing amount of a mixture of a polyalkylene glycol and an acid.

This application further relates to mixtures of the hereindisclosed polyalkylene glycols and acids, whereby granular formulations of the organothiophosphorus compounds, (e.g., S,S-dipropyl O-ethyl phosphorodithioate) using clay carriers deactivated with said mixtures, exhibit high storage stability. A particularly important use for such compositions is in corn rootworm control.

A non-exhaustive list of suitable polyalkylene glycols include ethylene glycol, propylene glycol, butylene glycol, diethylene glycol, triethylene glycol, isobutylene glycol, t-butylene glycol, polyethylene glycol and the like; and for example, any such glycols having from 2 to 12 carbon atoms.

In regard to the acid component, organic acids and inorganic acids may be used, and, in more specific embodiments, acids such as acetic acid, acrylic acid, ethylhexanoic acid, formic acid, phosphoric acid, and others.

The compositions in accordance with this invention generally contain from about 2 to about 10 wt. % or more preferably 3 to 5 wt. % of each of the stabilizing agents, i.e., of the glycol and acid based, on the total weight of the composition.

The organothiophosphorus compounds useful for the compositions embodied herein may be conveniently prepared in accordance with the disclosure of U.S. Pat. No. 3,268,393, incorporated herein by reference.

Exemplary organothiophosphorus compounds include S,S-dipropyl O-methyl phosphorodithioite; S,S-dipropyl O-methyl phosphorodithioate; S,S-dipropyl O-ethyl phosphorodithioate and S,S-dibutyl O-methyl phosphorodithioate. S,S-dipropyl O-ethyl phosphorodithioate is a particularly preferred embodiment.

This application is further directed to a method of controlling various insects, nematodes, mites, symphylans and especially corn rootworm comprising applying to said pest or its environment an effective amount of for example a granular formulation of said organothiophosphorus compound and particulate clay carrier in combination with a mixture of polyalkylene glycol and acid in accordance with the hereinembodied invention.

The amounts of the various components utilized in the instant compositions may vary considerably depending for example on whether they are applied as dusts or sprays, the type of insect and its normal habitat, etc. Therefore, the following examples will specifically illustrate concentrations of the active pesticidal ingredients that are representative of the effective ranges only and are not intended to unnecessarily limit the invention. Generally speaking and as stated supra the compositions according to this invention will contain from about 2 to about 10 wt. % or 3 to about 5 wt. % of each of the joint stabilizing agents, that is of alkylene glycol and appropriate acid, with the remainder of the composition comprising the organothiophosphorus compound, the clay carrier and any other components commonly used by the art in such formulations.

As a general rule, acceptable clay carriers are those which are non-hygroscopic (to prevent caking) and substantially inert (to eliminate as much as possible undesirable adverse effects upon the formation itself and upon the environment to be treated). Some especially useful clay carriers are finely ground particulate kaolinite, bentonite, talc, attapulgite, florex, montmorillonite and the like. Preferred are attapulgite and montmorillonite clays.

EXAMPLE 1

PROPYLENE GLYCOL (5%) AS DEACTIVATOR

Propylene glycol (0.5g), boiled linseed oil (0.2g) and S,S-dipropyl O-ethyl phosphorodithioate (at least 95% purity) (1.1g) were dissolved in methylene chloride (50 ml), and attapulgite clay (8.2g) (30/60 mesh) was added portionwise to the stirred solution. Evaporation of the solvent left free-flowing granules which were found to have an initial assay of 10.9% S,S-dipropyl O-ethyl phosphorothioate (active component). The granules were then stored at 50° C. and portions were assayed periodically with the following results:

| Days | Assay of Active Component | % of Active Component Remaining |
|---|---|---|
| 0 | 10.9 | 100 |
| 7 | 10.1 | 93 |
| 21 | 9.2 | 84 |
| 42 | 8.6 | 79 |

EXAMPLE 2

ACETIC ACID (5%) AS DEACTIVATOR

A formulation was prepared as in Example 1, except that acetic acid (0.5g) replaced propylene glycol. The following results were obtained:

| Days at 50° C | % of Active Component Remaining |
|---|---|
| 0 | 100 |
| 7 | 96 |
| 21 | 87 |
| 42 | 82 |

EXAMPLE 3

PROPYLENE GLYCOL (5%) AND ACETIC ACID (5%) AS DEACTIVATOR SYSTEM

A formulation was prepared as in Example 1, except that acetic acid (0.5g) replaced the same weight of attapulgite clay. Results were:

| Days at 50° C | % of Active Component Remaining |
|---|---|
| 0 | 100 |
| 7 | 100 |
| 21 | 97 |
| 42 | 91 |

EXAMPLE 4

ILLUSTRATING THE USE OF THE MIXED DEACTIVATOR SYSTEM WITH OTHER CLAY CARRIERS

Formulations were prepared in the same manner as in Example 3, with clay carriers other than attapulgite. In this example the deactivator system was 3 wt. % propylene glycol (P.G.)3 wt. % acetic acid. The results are shown compared with the deactivator system of 5 wt. % propylene glycol as in Example 1.

| | Florex | Clay Oil-Dri Attapulgite | Oil-Dri Montmorillonite |
|---|---|---|---|
| % Of Original Remaining, using 5 wt. % P.G. as deactivator | 82* | 88 | 84 |
| % Of Original Remaining using 3 wt. % P.G. - 3 wt. % acetic acid as deactivator | 94 | 94 | 88 |

*All numbers refer to 42 days at 50° C.

EXAMPLE 5

ILLUSTRATING THE USE OF OTHER ACIDS IN PLACE OF ACETIC ACID IN THE MIXED DEACTIVATOR SYSTEM

Formulations were prepared as in prior examples, using attapulgite as the clay carrier with (1) 5 wt. % of an acid as deactivator system, (2) with 5 wt. % of propylene glycol as deactivator system, and (3) with a 3 wt. % - 3 wt. % mixed acid/propylene glycol deactivator system. Results are shown below:

| | 5% Acid Alone | 5% Glycol Alone | 3%—3% Mixed Deactivator System |
|---|---|---|---|
| % Of Original Remaining after 42 days at 50° C, using | | | |
| Acrylic Acid | 74 | 79 | 93 |
| Formic Acid | 72 | 79 | 83 |
| Ethylhexanoic | 68 | 79 | 93 |
| Phosphoric | 80 | 79 | 84 |

EXAMPLE 6

Granular formulations were prepared, in accordance with Example 3 of compositions of the mixed deactivator (stabilizing) system comprising 3 wt. % propylene glycol and 3 wt. % acetic acid with montmorillonite clay as carrier and applied under field conditions to corn plots to illustrate corn rootworm control:

| A.I. lb/[a] Acre | Rating of 10 Plants[b] After 10 Weeks | | | |
|---|---|---|---|---|
| | Group 1 | Group 2 | Group 3 | Aver. |
| 1 | 1.9 | 2.0 | 2.2 | 2.03 |
| 2 | 1.6 | 1.5 | 1.6 | 1.56 |
| Untreated | 4.2 | 3.8 | 4.3 | 4.1 |

| A.I. lb/ Acre | Larvae Remaining on Entire Plant After | | % Roots pruned[c] | Aver. Rating[b] 3 Groups After 8 Weeks Location | |
|---|---|---|---|---|---|
| | 7 wks. | 10 wks. | | 1 | 2 |
| 1 | 2.1 | 2.6 | 0 | 2.7 | 2.4 |
| Untreated | 10 | 6.25 | 92 | 5.5 | 5.4 |

[a]Active ingredient in lbs. per acre.
[b]Rating on a 1-6 scale; 1 = complete control, 6 = no control
[c]% roots pruned by rootworms on one node of plant after 5 weeks.

The Examples serve to illustrate that compositions, in accordance with this invention, containing the stated organothiophosphorus compounds have improved shelf-life and storage stability, and prolonged pesticidal effectiveness particularly against the difficult to control corn rootworm. For example as demonstrated herein above compositions in accordance with the invention effectively control corn rootworm after 8-10 weeks of use under field conditions.

It is understood that modifications of the preferred embodiments herein-described may be resorted to without departing from the spirit and scope of this invention. Such variations and modifications are within the scope and purview of the appended claims as one of ordinary skill in the art will readily understand.

What is claimed is:

1. A composition comprising an insecticidally and nematocidally effective amount of an organothiophosphorus compound having the following general formula:

$$(RS)_2P(O)OR'$$

wherein R' is selected from the group consisting of methyl and ethyl, R is selected from the group consisting of propyl and butyl when R' is methyl, and R is propyl when R' is ethyl, a solid particulate attapulgite clay carrier therefor and a mixture of from about 2 to 10 weight percent, by weight of the total composition, of propylene glycol and from about 2 to 10 weight percent, by weight of the total composition, of an acid selected from the group consisting of acetic acid, acrylic acid, ethylhexanoic acid, and formic acid; wherein said propylene glycol and said acid are present in equal weight amounts.

2. The composition of claim 1 wherein the acid is acetic acid.

3. A method for controlling insects and nematodes comprising applying to said insects and nematodes or to their environment an effective amount of a composition as defined in Claim 1.

4. The method of claim 3 wherein the acid is acetic acid.

5. A method for controlling corn rootworm which comprises applying to said corn rootworm or the environment thereof an effective amount of a composition as defined in claim 1.